April 18, 1939. J. W. SAVELY Plant Pat. 327

APPLE

Filed March 5, 1938

JAMES W. SAVELY
DISCOVERER

Robert T. Killman
ATTORNEY

Patented Apr. 18, 1939

Plant Pat. 327

UNITED STATES PATENT OFFICE

327

APPLE

James W. Savely, near Hendersonville, Tenn.

Application March 5, 1938, Serial No. 194,230

1 Claim. (Cl. 47—62)

My discovery relates generally to apple trees.

The original tree was discovered growing as a seedling, of unknown parentage, on my property located near the town of Hendersonville, Sumner County, Tennessee, Sixth Civil District, and has since been successfully asexually reproduced; the reproduced trees and their fruit maintaining the same novel characteristics as the original tree and its fruit.

Figure 1:
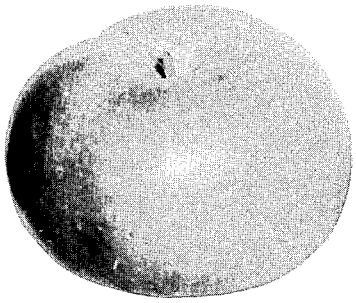

Figure 1 in the original drawing illustrates an average size apple of this tree showing the fruit as viewed from the base. The color is the same as in the Rhode Island Greening. Color is not a variation upon which my new variety of apple depends for patentability.

Figure 2:
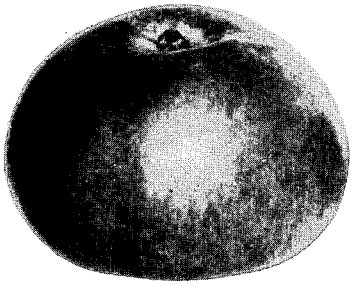

Figure 2 in the original drawing illustrates an average size apple of my new variety as viewed from the apex.

Figure 3:
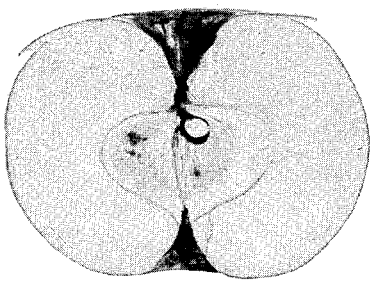

Figure 3 illustrates a vertical section of the apple showing the core and its parts.

I now refer in more detail to my new variety of apple tree and its fruit.

*The tree*

The tree is of medium size, strong and vigorous. It is generally of upright form, roundish to spreading. It is rapid growing, very productive and a regular bearer.

The trunk of the tree is of medium size, smooth, and of a light green color with a reddish overcast. The branches are of medium size, smooth, and of a light green color. Lenticels are numerous and of medium size. The leaves of the tree are of medium size averaging about 2½ inches in width and about 3¼ inches in length, and are of a dark green color. The shape of the leaves is broad, roundish, margins serrate to dentate, while the petiole is of medium size. The trees bear young. The terminals of the previous season produce fruit. The fruit hangs well on the tree.

*Flowers*

The flowers are of medium size, of a light pink color and bloom about mid-season.

*Fruit*

The fruit is oblate, uniform, symmetrical and averages 2¾ to 3 inches in diameter. The stem is medium to short in length and of medium size.

The skin of the fruit is thin to very thin, smooth, slightly waxy, and is of a pale green color with a buttermilk overspread, and occasionally with a slight blush.

The flesh is crisp, juicy, of a greenish-white color and is acid to sub-acid in flavor. The cavity is acute to acuminate, deep and of medium width, slightly lipped, of a lighter green color with russet rays wholly within the cavity.

The calyx is closed to partly open; the lobes are basal and divergent; the basin is shallow and of medium width; the core is in the median position, open, and small in size; the core lines are clasping; the calyx tube is cone shaped; and the seeds are acuminate to acute and are slightly tufted. The fruit is of good quality, is very juicy, is especially suitable for cooking purposes, is of good keeping quality, and is suitable for shipping.

As compared with the Rhode Island Greening, the variety which my new apple most closely resembles, its flavor is distinctly more acid. The ripening season of my new variety is late July and early August.

The tree and its fruit above described may of course vary in slight details depending on the climatic and soil conditions under which they are grown.

Having thus described my discovery, I claim:

The apple tree variety herein described characterized by the acid flavor and early ripening of the fruit.

JAMES W. SAVELY.